(12) United States Patent
Ravetch et al.

(10) Patent No.: US 7,038,031 B1
(45) Date of Patent: May 2, 2006

(54) DNA ENCODING FCγR RECEPTOR PROTEIN ON NK CELLS

(75) Inventors: Jeffrey V. Ravetch, New York, NY (US); Bice Perussia, Philadelphia, PA (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 08/480,819

(22) Filed: Jun. 7, 1995

Related U.S. Application Data

(63) Continuation of application No. 08/254,474, filed on Jun. 6, 1994, now abandoned, which is a continuation of application No. 08/133,777, filed on Oct. 8, 1993, now abandoned, which is a continuation of application No. 07/808,059, filed on Dec. 12, 1991, now abandoned, which is a continuation of application No. 07/387,758, filed on Jul. 28, 1989, now abandoned.

(51) Int. Cl.
*C07H 21/04* (2006.01)
(52) U.S. Cl. .................. 536/23.5; 435/325; 435/252.3; 435/320.1
(58) Field of Classification Search .............. 435/91, 435/320, 317.1, 240.2, 320.1, 172.3, 91.1, 435/91.4, 91.32, 252.3, 325; 935/2, 4, 9, 935/11, 22, 23, 70; 536/27, 23.1, 23.5
See application file for complete search history.

(56) References Cited

U.S. PATENT DOCUMENTS 5,976,831 A * 11/1999 Peltz ......................... 435/69.1

FOREIGN PATENT DOCUMENTS

WO 8803172 * 5/1988

OTHER PUBLICATIONS

Scallon et al. 1989 Proc. Natl. Acad. Sci. USA. 86, 5079-5083.*
Stuart etal. 1987. J. Exp. Med. 166, 1668-1684.*
Peltz etal. 1989. Proc. Natl. Acad. Sci. USA. 86, 1013-1017.*
Simmons etal. 1988 Nature 333, 568-570.*
Weinshank etal. 1988, J. Exp. Med. 167, 1909-1925.*
Perussia etal. 1989, J. Exp. Med. 170, 73-86.*
Kinet, etal. 1987, Biochemistry 26, 4605-4610.*
Ravetch etal. 1989, J. Exp. Med. 170, 481-497.*
Miller, J. Immunol. 134(6), 4212-4217, Jun. 1985.*

* cited by examiner

*Primary Examiner*—Brenda Brumback
*Assistant Examiner*—Jon M Lockard
(74) *Attorney, Agent, or Firm*—Darby & Darby

(57) ABSTRACT

The present invention provides DNA encoding an FcγRIII (CD16) receptor protein expressed on NK cells. The invention also provides a stable cell line expressing the FcγRIII (CD16) from NK cells. Further provided is a method for determining the presence of HIV-enhancing antibodies and a method for treating an HIV-infected subject.

14 Claims, 10 Drawing Sheets

FIG. 3B

```
III-1 TCTTTGGTGACTTGTCCACTCCAGTGTGGCATCATGTGGCAGCTGCTCCTCCCAACTGCTCTGCTACTTCTAGTT 75
III-2 ---------------------------------------------------------------------------

III-1 TCAGCTGGCATGCGGACTGAAGATCTCCCAAAGGCTGTGGTGTTCCTGGAGCCTCAATGGTACAGCGTGCTTGAG 150
III-2 ------------------------------------------------------------G-----C---

III-1 AAGGACAGTGTGACTCTGAAGTGCCAGGGAGCCTACTCCCCTGAGGACAATTCCACACAGTGGTTTCACAATGAG 225
III-2 ---------------------------------------------------------------------------

III-1 AGCCTCATCTCAAGCCAGGCCTCGAGCTACTTCATTGACGCTGCCACAGTCAACGACAGTGGAGAGTACAGGTGC 300
III-2 ---------------------------------------------G----------------------------

III-1 CAGACAAACCTCTCCACCCTCAGTGACCCGGTGCAGCTAGAAGTCCATATCGGCTGGCTGTTGCTCCAGGCCCCT 375
III-2 ---------------------------------------------------------------------------

III-1 CGGTGGGTGTTCAAGGAGGAAGACCCTATTCACCTGAGGTGTCACAGCTGGAAGAACACTGCTCTGCATAAGGTC 450
III-2 ---------------------------------------------------------------------------

III-1 ACATATTTACAGAATGGCAAAGACAGGAAGTATTTTCATCATAATTCTGACTTCCACATTCCAAAAGCCACACTC 525
III-2 ---------------G-----------------------------T----------------------------

III-1 AAAGATAGCGGCTCCTACTTCTGCAGGGGGCTTGTTGGGAGTAAAAATGTGTCTTCAGAGACTGTGAACATCACC 600
III-2 -----C------------------------T-------------------------------------------

III-1 ATCACTCAAGGTTTGGCAGTGTCAACCATCTCATCATTCTCTCCACCTGGGTACCAAGTCTCTTTCTGCTTGGTG 675
III-2 ------------------------------------T-------------------------------------

III-1 ATGGTACTCCTTTTTGCAGTGGACACAGGACTATATTTCTCTGTGAAGACAAACATTTGAAGCTCAACAAGAGAC 750
III-2 -----------------------------------------------------C--------------------

III-1 TGGAAGGACCATAAACTTAAATGGAGAAAGGACCCTCAAGACAAATGACCCCCATCCCATGGGAGTAATAAGAGC 825
III-2 --------------T------------------------------------------G-----------

III-1 AGTGGCAGCAGCATCTCTGAACATTTCTCTGGATTTGCAACCCCATCATCCTCAGGCCTCTC 887
III-2 ---A---------------------------------------------------------

III-1 MWQLLLPTALLLLVSAGMRTEDLPKAVVFLEPQWYSVLEKDSVTLKCQGAYSPEDNSIQWFHNESLISSQASSYF 75
III-2 ----------------------------------------R---------------------------------

III-1 IDAATVNDSGEYRCQTNLSTLSDPVQLEVHIGWLLLQAPRWVFKEEDPIHLRCHSWKNTALHKVTYLQNGKDRKY 150
III-2 ------D--------------------------------------------------------------G---

III-1 FHHNSDFHIPKATLKDSGSYFCRGLVGSKNVSSETVNITITQGLAVSTISSFSPPGYQVSFCLVMVLLFAVDTGL 225
III-2 -------Y------------F----------------------F-----------------------

III-1 YFSVKTNI*                    233
III-2 --------RSSTRDWKDHKFKWRKDPQQK*  254
```

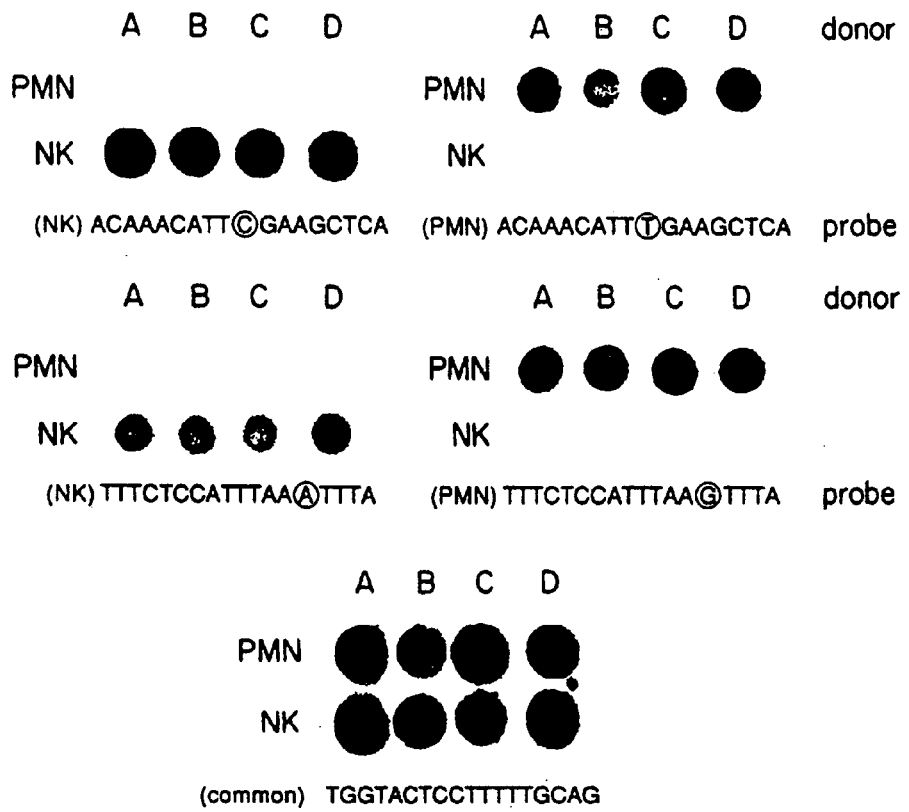

FIG. 5
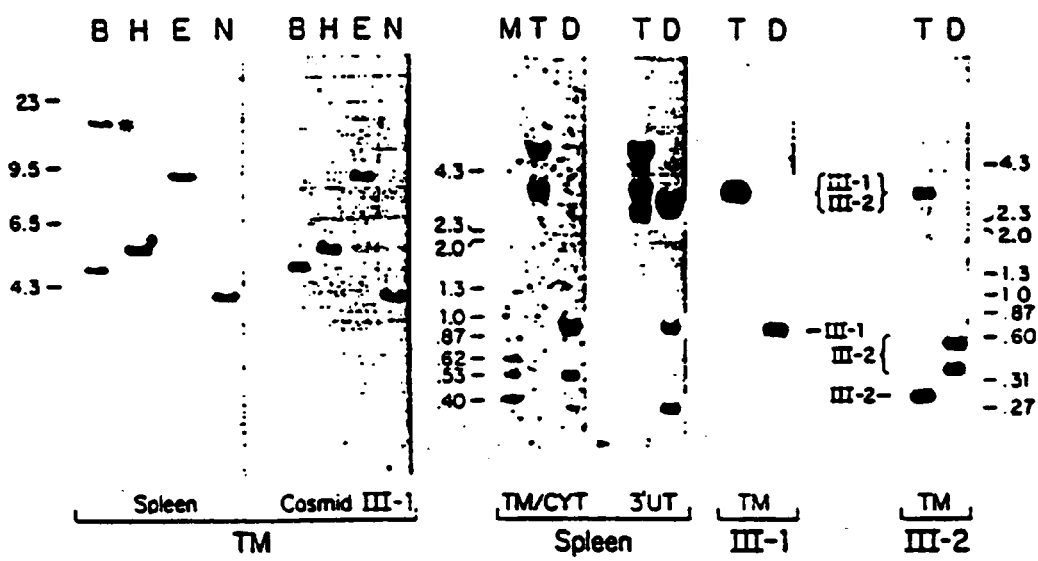
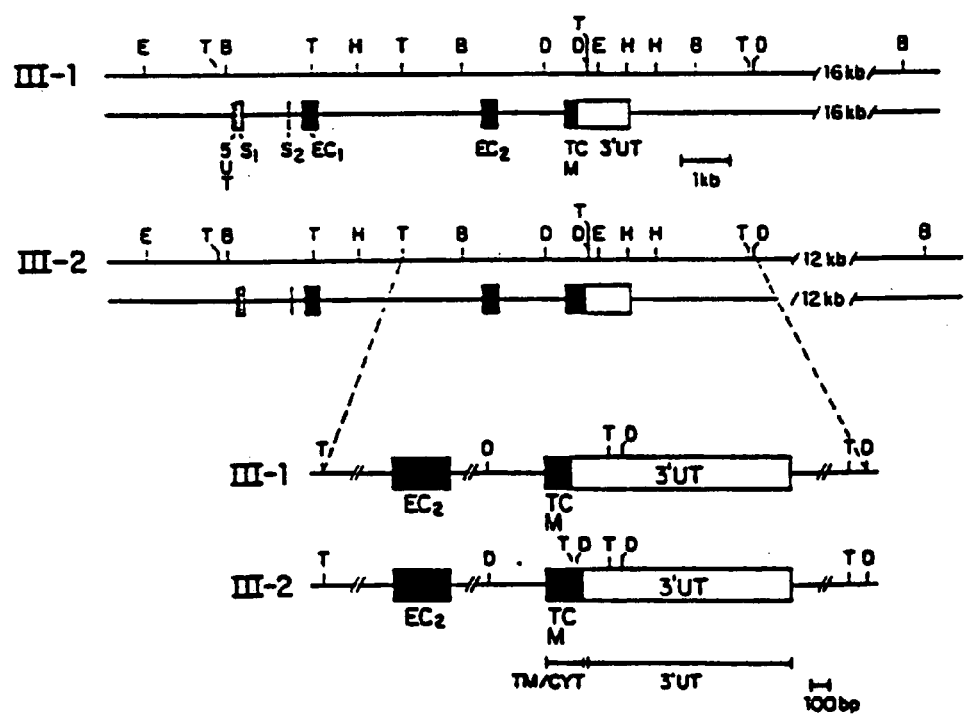

```
              G   L   A   V   S   T   I   S   S   F   S   P   P   G   Y   Q   V   S   F   C   L   V
III-1         GTTGGCAGTGTCAACCATCTCATCATTCTCTCCACCTGGGTACCAAGTCTCTTTCTGCTTGGTG
PMN           .........GUUUGGCAGUGUCAGUUCAGUUCAGUUCUCUCCACCUGGGUACCAAGUCUCUUUCUGCUUGGUG
III-2         GTTGGCAGTGTCAACCATCTCATCATTCTCT(T)CCACCTGGGTACCAAGTCTCTTTCTGCTTGGTG
NK            .........GUUUGGCAGUGUCAGUUCAGUUCAGUUCUCCACCUGGGUACCAAGUCUCUUUCUGCUUGGUG
                                                    F
```

```
              M   V   L   F   A   V   D   T   G   L   Y   F   S   V   K   T   N   I   *
III-1         ATGGTACTCCTTTTGCAGTGGACACAGGACTATATTTCTGTGAAGACAAACATTTGAAGCTCAACAAGAGAC
PMN           AUGGUACUCCUUUUGCAGUGGACACAGGACUAUAUUUCUGUGAAGACAAACAUUUGAAGCUCAACAAGAGAC
III-2         ATGGTACTCCTTTTGCAGTGGACACAGGACTATATTTCTGTGAAGACAAACATT(C)GAAGCTCAACAAGAGAC
NK            AUGGUACUCCUUUUGCAGUGGACACAGGACUAUAUUUCUGUGAAGACAAACAUUCGAAGCUCAACAAGAGAC
                                                                          R   S   S   T   R   D
```

```

III-1         TGGAAGGACCATAAACTTAAATGGAGAAAGGACCCTCAAGACAAATGACCCCCATCCCATGGGAGTAATAAGAGC
PMN           UGGAAGGACCAUAAACUUAAAUGGAGAAAGGACCCUCAAGACAAAUGACCCCCAUCCCAUGGGAGUAAUAAGAGC
III-2         TGGAAGGACCATAAA(T)TTAAATGGAGAAAGGAAGGACCCTCAAGACAAATGACCCCCATCCCATGGG(G)GTAATAAGAGC
NK            UGGAAGGACCAUAAAUUUAAAUGGAGAAAGGAAGGACCCUCAAGACAAAUGACCCCCAUCCCAUGGGGGUAAUAAGAGC
              W   K   D   H   K   F   K   W   R   K   D   P   Q   D   K   *
```

```
III-1         AGTGGCAGCAGCATCTCTGAACA......
PMN           AGUGGCAGCAGCAUCUCUGAACA......
III-2         AGT(A)GCAGCAGCATCTCTGAACA......
NK            AGU(A)GCAGCAGCAUCUCUGAACA......
```

FIG. 7A

| | Structure of Gene | Expression Efficiency (%) -γ | Expression Efficiency (%) +γ | PIPLC Sensitivity (%) +PIPLC/−PIPLC | Membrane Form |
|---|---|---|---|---|---|
| III-1 | | 100 | 112 | 5 | PI |
| III-2 | | <1 | 55 | 92 | TM |
| III-1(F) | | <1 | 111 | 125 | TM |
| III-2(S) | | 95 | 65 | <1 | PI |
| 1-2(K) | | 92 | 94 | 10 | PI |
| 1-2(A) | | <1 | 107 | 76 | TM |
| 1-2(P) | | <1 | 74 | 105 | TM |
| 2-1(K) | | <1 | 65 | 89 | TM |

FIG. 7B

|  |  |  |  |  |
|---|---|---|---|---|
| 2-1(A) | R—S—D—I—G—F=S≈≈≈D≈ | 87 | 65 | <1 | PI |
| 2-1(P) | R—S—D—I—G—L=V=S≈≈≈D≈ | 101 | 104 | 2 | PI |
| III-1(V) | R—N—D—V—G—D—H—V=S≈≈≈V≈ | 73 | 71 | 1 | PI |
| III-2(V) | R—S—D—I—G—L=F=F≈≈≈ | 4 | 34 | 99 | TM |

DNA ENCODING FCγR RECEPTOR PROTEIN ON NK CELLS

This is a continuation of U.S. Ser. No. 08/254,474, filed Jun. 6, 1994 (now abandoned), which is a continuation of U.S. Ser. No. 08/133,777, filed Oct. 8, 1993 (now abandoned), which is a continuation of U.S. Ser. No. 07/808,059, filed Dec. 12, 1991 (now abandoned), which is a continuation of U.S. Ser. No. 07/387,758, filed Jul. 28, 1989 (now abandoned), the contents of which are hereby incorporated by reference.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

A low affinity receptor for IgG immune complexes, FcγRIII(CD16), is expressed on human natural killer (NK) cells and macrophages as an integral membrane glycoprotein anchored through a transmembrane peptide; on polymorphonuclear neutrophils (PMN) the receptor is anchored through a phosphatidylinositol (PI) linkage. The protein on NK cells macrophages has a molecular mass 6–10 kDa larger than that on PMN, and, unlike the latter, is resistant to PI-specific phospholipase C (PI-PLC). FcγRIII(CD16) transcripts isolated from PMN and NK cells of single donors revealed multiple single nucleotide differences, one of which converts an in frame UGA termination codon to CGA codon. The resulting open reading frame encodes a longer cytoplasmic domain for FcγRIII(CD16) in NK cells, contributing to its transmembrane anchor. Two nearly identical, linked genes which encode these transcripts have been cloned for FcγRIII(CD16), one of which (III-1) is allelic for NA-1 and NA-2. The allelic sites have been mapped to two single nucleotides in the extracellular domain. These genes are transcribed in a cell-type specific fashion to generate the alternatively anchored forms of this receptor.

Receptors for the Fc fragment of immunglobulin G (FcγR) couple the humoral and cellular immune responses by targetting immune complexes to effector cells. Multiple FcγRs exist, which differ in ligand affinity, cellular distribution and effector function (reviewed in 1). Detailed characterization of the FcγRs in both mouse and human has begun to address the molecular basis for the diversity of cellular responses triggered by a common ligand. The binding of immune complexes is mediated by extracellular immunoglobulin-like domains which are conserved among many FcγRs. The functional consequence of this binding, on the other hand, is mediated by the divergent transmembrane and cytoplasmic domains which are the result of gene duplication as well as alternative mRNA splicing. In the mouse the low affinity, immune complex IgG Fc receptors (FcγRII) are encoded by two genes, α and β (2, 3, 4). cDNA sequence analysis predicts that these receptors are similar integral membrane glycoproteins with 180 amino acid extracellular domains, single transmembrane spanning domains of 20 amino acids and intracytoplasmic domains which very from 26 amino acids for α to 93 amino acids for the larger spliced form of β, $β_1$. α is expressed on macrophages and NK cells, while β is expressed on lymphocytes and macrophages and displays cell type-specific alternative mRNA splicing of its cytoplasmic domains. The human homologues of these receptors include a minimum of three genes for FcγRII (CD32) (Ravetch, et al. unpublished) and two genes for FcγRIII(CD16) (this report). cDNA clones have been isolated for FcγRII (CD32) (5,6, Ravetch, et al. unpublished) and FcγRIII(CD16) (7,8).

FcγRIII(CD16) is expressed on NK cells, macrophages and PMN (9,10,11). Two alleles, NA-1 and NA-2, have been described for this receptor on PMN. It has been shown to mediate antibody-dependent cellular cytotoxicity (ADCC) by NK cells (12) where it represents the only FcγR. On PMN, FcγRIII(CD16) has been proposed to act together with FcγRII (CD32) to mediate effector functions (13, 14). Anti-FcγRIII(CD16) antibodies inhibit ADCC and immune complex binding (9,10,15) on both PMN and NK cells. Recently it has been shown that FcγRIII(CD16) is anchored through a glycosyl-phosphatidylinositol (PI) linkage on PMN (13,16). The first evidence for an alternative membrane-associated form for FcγRIII(CD16) came from the study of patients with paroxysmal nocturnal hemoglobinuria (PNH). In that acquired disorder, a defect in the attachment of the PI tail in hematopoietic precursor cells results in the selective deficiency of PI-anchored proteins (reviewed in 17). FcγRIII(CD16) is expressed at 10% of normal levels on PMN in those patients, but its expression on macrophages and NK cells is unaffected (16,18), indicating that NK cells and macrophages express an alternative anchored form of FcγRIII(CD16) which is presumably transmembrane. cDNA clones for FcγRIII(CD16) have been isolated from placental and neutrophil libraries (7,8). Those clones predict a sequence for an FcγRIII(CD16) protein which contains two canonical immunoglobulin-like extracellular domains, a weakly hydrophobic transmembrane domain and a short (4 amino acid) cytoplasmic domain, features characteristic of PI-linked molecules (17,19). Transfection of those clones resulted in the appearance of PI-linked molecules on COS cells; thus it appeared unlikely that these cDNA clones encoded a transmembrane form of FcγRIII(CD16).

It has been shown that antibody-dependent enhancement (ADE) of infection by human immunodeficiency virus (HIV) of macrophages is mediated by FcγRIII(CD16) (40). In the presence of enhancing antibodies, HIV can infect a cell independently of the CD4 protein. The FcγRIII(CD16) receptor mediates uptake of HIV-enhancing antibody complexes into human macrophages.

The inventors have demonstrated that the FcγRIII(CD16) molecule indeed exists in two alternative membrane-anchored forms—a PI-linked form on PMN and a larger PI-PLC resistant transmembrane protein on NK cells. To establish the molecular basis for this difference, FcγRIII(CD16) encoding RNA from NK cells and PMN of single individuals homozygous for either NA-1 or NA-2 were analyzed and found to differ by multiple single nucleotide substitutions. One of these non-allelic changes results in the expression of a transcript in NK cells in which a CGA codon replaces a UGA termination codon thereby extending the reading frame for the cytoplasmic domain of this FcγRIII (CD16) by 21 amino acids, which are homologous to the murine FcγRIIα cytoplasmic domain. Two distinct genes encoding FcγRIII(CD16) have been cloned and sequenced. Cell-type specific expression of these linked genes accounts for the NK cell and PMN transcripts and the alternatively-anchored forms of this receptor.

SUMMARY OF THE INVENTION

The present invention provides an isolated nucleic acid molecule encoding an Fc receptor protein which is expressed on NK cells and macrophages.

The present invention also provides an isolated nucleic acid molecule encoding an Fc receptor protein having an amino acid sequence substantially identical to an Fc receptor protein present on NK cells and macrophages.

Further provided is a recombinant cloning vector which comprises suitable carrier DNA and DNA encoding an Fc receptor protein expressed on NK cells. A host cell comprising the recombinant cloning vector is also provided.

The invention also provides a cell line capable of stably expressing an Fc receptor protein which is expressed on NK cells.

The present invention also provides a method of determining the presence of HIV-enhancing antibodies in a fluid sample of an HIV-infected subject. The method comprises contacting the sample with the stably expressing cell of the invention and detecting infection of the cell by HIV.

Also provided is a method of determining whether an HIV-infected subject is amenable to CD4 therapy. This method comprises determining the presence of HIV-enhancing antibodies in a fluid sample from the subject, the absence of HIV-enhancing antibodies in the sample indicating that the subject is amenable to CD4 therapy.

Further provided is a method of treating an HIV-infected subject. This method which comprises determining whether the subject is amenable to CD4 therapy and administering CD4 therapy to a subject determined to be amenable to CD4 therapy.

Buffy coat cells (left panels), cultures NK cells and PMN (right panels) were treated with PI-PLC and tested for surface expression of the indicated antigens by indirect immunofluorescence. PBL and PMN in the buffy coat were gated on the basis of their forward and right angle light scatter and fluorescence was measured separately in each region. The histograms in each panel represent intensity of fluorescence: _____, untreated cells; -----, PI-PLC-treated cells. x axis, intensity of fluorescence (log scale); y axis, number of cells. The experiment on buffy coat cells is representative of 2, those on purified NK cells and PMN are representative of 4 performed.

Figure 2A:
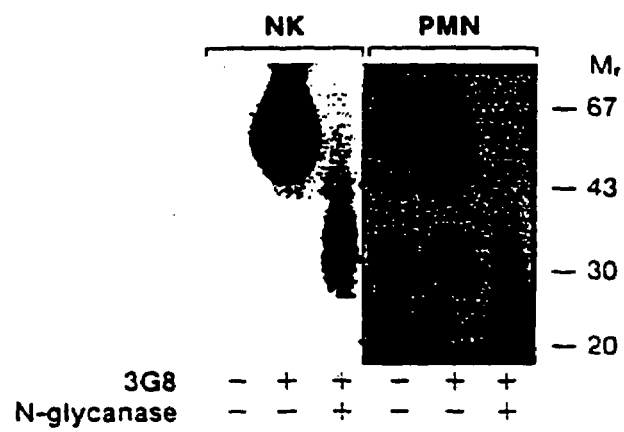
Figure 2B:
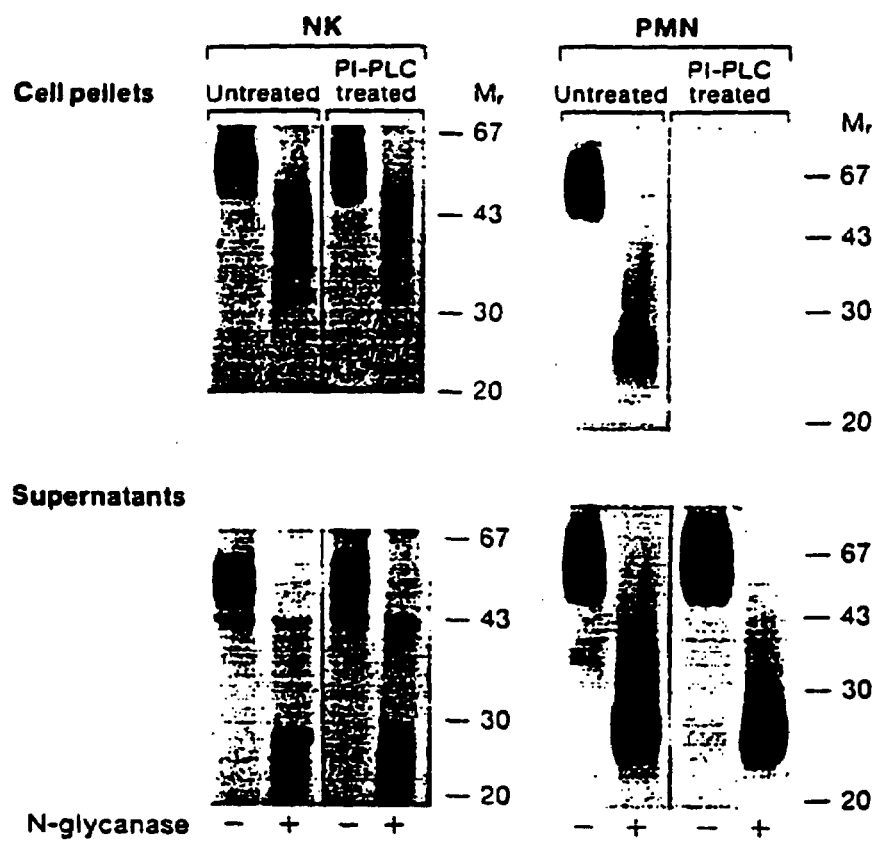

FIG. 2. PI-PLC-sensivity and N-glycanase digestion of FcγRIII(CD16).

Cultured NK cells purified as described in Materials and Methods and PMN freshly separated from peripheral blood were labeled with $^{125}$I. After labelling, the cells were divided into three aliquots: one of these (control) was processed immediately, one (untreated) was incubated at 37° C. in medium, and one (treated) was incubated in the presence of PI-PLC (1:200 dilution, 45 min, 37° C.). Antibody 3G8 was used to precipitate FcγRIII(CD16) from the different cell pellets and from their supernatants, as indicated. Immunoprecipitates, untreated or treated with N-glycanase (20 U/ml, 18 h, 37° C.) were analyzed in SDS-10% PAGE. Positions of the molecular weight markers run on the same gels are indicated (Mr×10$^{-3}$). A) 3G8 immunoprecipitates from control cells. In panel B, lanes labelled cells were exposed 3× longer than the corresponding supernatant lanes.

FIG. 3. Sequence analysis of FcγRIII(CD16) transcripts in PMN and NK cells.

A) RNA extracted from the indicated cells of a single individual were converted to cDNA using oligo 465 and amplified by PCR using oligo 466 (see Materials and Methods). Oligo 473 was end-labelled with $^{32}$P and used to generate an extension product from the amplified cDNA, gel purified and sequenced by the chemical degradation method (28). Identical results were obtained using oligos 485/494 on total RNA, extending with oligo 466 or 473. Sequences were confirmed on the opposite strand using oligos 491, 465 or 474. Asterisks indicate nucleotide differences between the cell types. The effect of these sequence changes on the translation of the FcγRIII(CD16) transcript is indicated. The lanes of the sequencing gels are (left to right): G, A>C, T+C and C. B) Nucleotide sequence of cDNA for FcγRIII(CD16) obtained from NK cells and PMN of an NA-2/NA-2 individual. III-1 indicates the PMN sequence; III-2 the NK cell sequence. Identical nucleotides are indicated by dashes. III-1 nucleotides indicated in bold-face are allelic in NA-1/NA-1; overlined nucleotides (227 and 349) determine the NA-2 and NA-1 reactivities of PMN FcγRIII(CD16), respectively. The predicted amino acid sequence is shown below with the hydrophobic core of the signal sequence and transmembrane domain overlined. N-linked glycosylation sites are underlined. The extended reading frame for the NK cell transcript (III-2) is indicated in bold-face, as are the amino acid differences.

FIG. 4. Oligonucleotide hybridization of PCR-amplified cDNA of NK cells and PMN.

RNA extracted from NK cells or PMN of single individuals was converted to cDNA and amplified using oligos 465/466, spotted on nitrocellulose and hybridized with end-labelled, NK-specific oligos 488 and 489 or PMN specific oligos 474 and 490 or the FcγRIII(CD16) common oligo 473. Four donors were studied, indicated A–D. The single nucleotide difference in each oligo is indicated.

FIG. 5. Two genes encode FcγRIII(Cd16): III-I and III-2.

Upper) Southern blot analysis of spleen DNA or DNA derived from clones of each gene as indicated. The blots were probed with $^{32}$P-labelled probes as indicated under each autoradiograph. The 18 kb BamH1 fragment detected with the TM probe, encoded on the III-2 gene is denoted with an asterisk. An arrow indicates the 280 bp Taq I fragment derived from the III-2 gene. The Taq and Dra experiments were resolved on 1.2% agarose gels to optimize the separation of small fragments, the blots marked spleen were probed first with the TM probe, stripped and reprobed with the 3'UT probe. Lower) Restriction maps of the two FcγRIII(CD16) genes. The exon-intron structure of each gene is indicated, as determined by DNA sequence analysis. The region corresponding to the TM-CYT-3'UT exon is expanded to indicate the position of the Taq I and Dra I sites generated in III-2 by the nucleotide differences between these genes (these sites are not indicated for III-2 on the upper map for clarity). Probes used in the study are indicated below the maps. E=EcoR1, B=BamH1, H=Hind III, T=Taq I, D=Dra I, N=NcoI, M=labelled markers. The restriction maps are not complete for the sequences flanking these genes 5' of the signal exon and 3' of the 3'UT exon.

FIG. 6. Sequence comparison of FcγRIII(CD16) transcripts in NK cells, PMN and genomic DNA.

A) Nucleotide sequence data is shown for the III-1 and III-2 genes and their deduced transcripts for the transmembrane/cytoplasmic/3' untranslated exon (indicated schematically at the top of the figure with relevant amino acids numbered) beginning at nucleotide 611 [numbering according to the published cDNA sequence (7)], which is the first nucleotide of this exon and extending to nucleotide 848. The genomic sequences were obtained independently from the cloned FcγRIII(CD16) genes isolated as described (see text and Methods). Positions where the sequences were found to differ are circled in the III-2 sequence. The predicted translation is indicated, with the extended reading frame for III-2 gene and the NK cell transcript indicated in bold-face type. B) Sequence alignment of the predicted carboxy-terminus of FcγRIII(CD16) in NK cells compared to the murine homologue, FcγRIIα, using the fastp algorithm (37). Two dots indicate identity, single dots indicate changes which arise by single nucleotide substitutions. The transmembrane domain is indicated.

FIG. 7. Effect of various amino acid substitutions between FcγRIII-1 and FcγRIII-2.

Portions of the sequences encoding each of the III-1 and III-2 genes, respectively, were substituted with sequences from corresponding portions of the other gene. The effect of the resulting amino acid changes on expression efficiency, PI-PLC sensitivity, and membrane-anchorage is shown.

Figure 8:
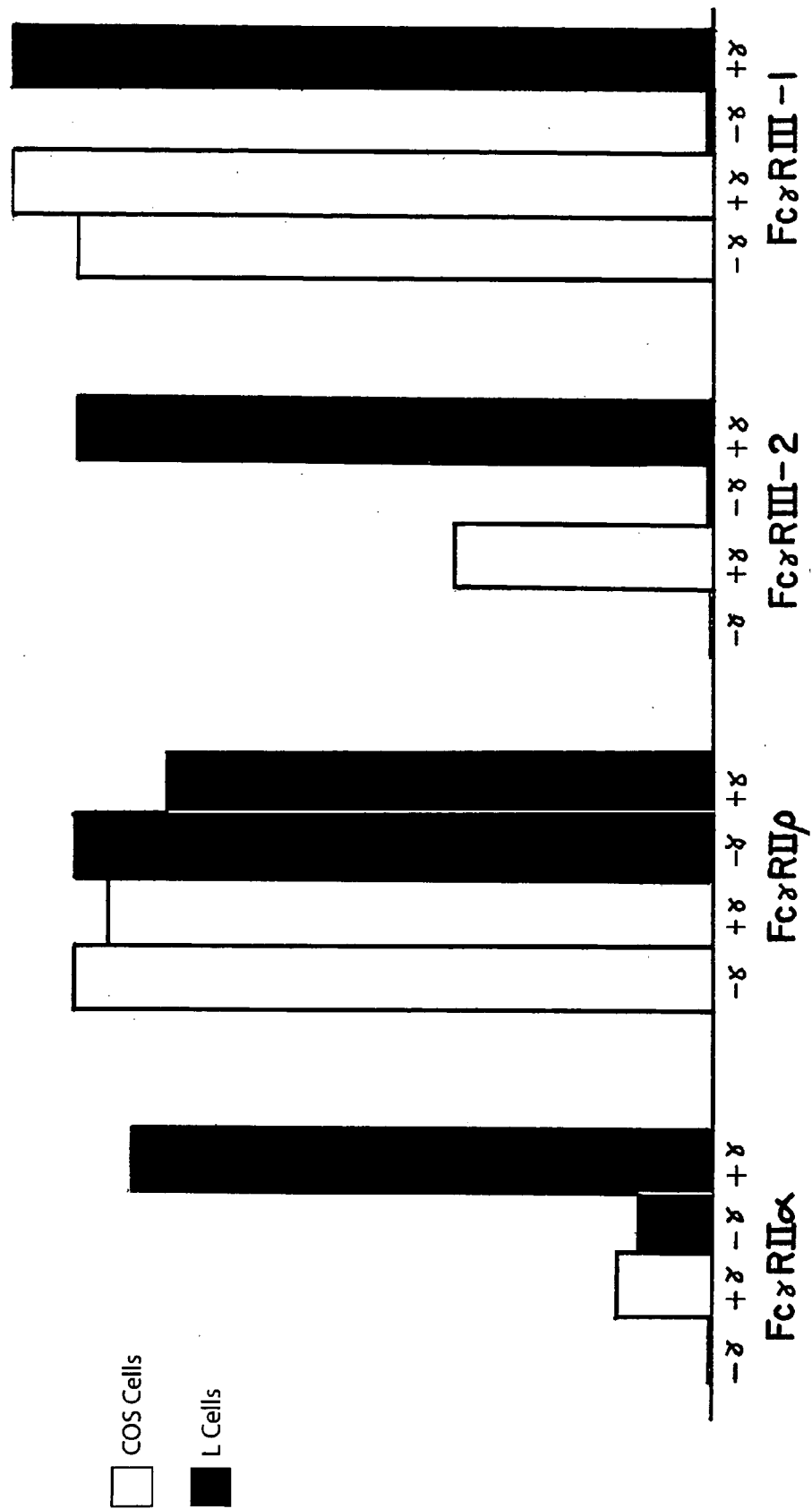

FIG. 8. Effect of FcεRIγ subunit on FcγR Expression.

Expression of various FcγRs was observed in transfected monkey COS and mouse L-cells. Mouse FcγRII α and human FcγRIII-2 were expressed efficiently only in the presence of the γ subunit of FcεRI.

DETAILED DESCRIPTION OF THE INVENTION

In the description of the invention which follows, HIV-enhancing antibodies means antibodies which mediate infectivity of human immunodeficiency virus (HIV), or are responsible for antibody-dependent enhancement (ADE) of HIV infection, and are directed against an FcγRIII(CD16) receptor. CD4 molecule means the entire CD4 molecule or any fragment thereof, including soluble fragments thereof, and includes the whole CD4 molecule and fragments thereof alone or linked to any other molecule or compound. CD4 therapy means administering any CD4 molecule to an HIV-infected subject.

The present invention provides an isolated nucleic acid molecule encoding an Fc receptor protein which is expressed on NK cells. The nucleic acid may be a cDNA or an mRNA. In one embodiment of the invention, the nucleic acid molecule encodes an Fc receptor protein having an amino acid sequence substantially identical to an Fc receptor protein expressed on NK cells. In a further embodiment, the nucleic acid molecule is a DNA molecule having the nucleotide sequence set forth in FIG. 3B and designated III-2.

The invention further provides an isolated Fc receptor protein which is expressed on NK cells. In one embodiment, the Fc receptor protein is one which is expressed on human NK cells. In a further embodiment, the Fc receptor protein has the acid amino sequence set forth in FIG. 3B and designated III-2.

Further provided is a recombinant cloning vector which comprises suitable carrier DNA and DNA encoding an Fc receptor protein expressed on NK cells. In a preferred embodiment of the invention, the DNA encoding an Fc receptor protein on NK cells has the nucleotide sequence set forth in FIG. 3B and is designated III-2. In another embodiment, the cloning vector is a plasmid. In a futher embodiment, the plasmid is pcEXV-3. A host cell comprising the recombinant cloning vector is also provided.

The invention also provides a cell line capable of stably expressing an Fc receptor protein which is expressed on NK cells.

The invention also provides a cell useful for determining the presence of HIV-enhancing antibodies in an HIV-infected subject. The cell line is capable of stably expressing an Fc receptor protein which is expressed on NK cells and macrophages, and comprising suitable carrier DNA and DNA encoding an Fc receptor protein which is expressed on NK cells and macrophages.

The present invention also provides a method of determining the presence of HIV-enhancing antibodies in a fluid sample of an HIV-infected subject. The methods comprises contacting the sample with the stably expressing cell of the invention and detecting the infection of the cell by HIV.

Also provided is a method of determining whether an HIV-infected subject is amenable to CD4 therapy. This method comprises determining the presence of HIV-enhancing antibodies in a fluid sample from the subject, the absence of HIV-enhancing antibodies in the sample indicating that the subject is amenable to CD4 therapy.

Further provided is a method of treating an HIV-infected subject. This method which comprises determining whether the subject is amenable to CD4 therapy and administering CD4 therapy to a subject determined to be amenable to CD4 therapy.

Materials and Methods

Cell lines. The human B lymphoblastoid cell line RPMI-8866, and the monoclonal antibody-producing hybrid cell clones were maintained in culture in RPMI-1640 (Flow Laboratories, Inc., Rockville, Md.) supplemented with 10% fetal bovine serum (FBS, Flow Laboratories). All cell lines were free of mycoplasma contamination.

Monoclonal and polyclonal antibodies. The monoclonal antibodies used in this study, their origin and specificity have been previously described (10, 20). Anti-CD16 monoclonal antibodies were: B73.1 (IgG1) produced and characterized in our laboratory (10), 3G8 (9) (IgG1) produced from cells kindly provided by Dr. J. Unkeless (Mount Sinai Medical School, New York, N.Y.) and CLB-Gran 11 (21), detecting the NA-1 alloantigen on PMN and GRM1, detecting the NA-2 antigen (kindly provided by F. Garrido). TS2/9 (anti-LFA-3) (22) was kindly provided by T. Springer (Harvard Medical School, Boston, Mass.). IgG were purified from ascites and labeled with biotin according to routine procedures. The polyclonal fluorescein isothiocyanate (FITC)-labeled goat F(ab')$_2$ anti-mouse Ig was purchased from Cooper (Malvern, Pa.). The goat anti-mouse IgG used to prepare erythrocytes (E) for indirect rosetting was produced in our laboratory, absorbed on human IgG, and affinity purified on mouse IgG-Sepharose 4B column (Pharmacia Fine Chemicals, Uppsala, Sweden).

Peripheral blood leukocytes, Natural Killer (NK) cells, polymorphonuclear granulocyte (PMN) and macrophage preparations. Venous peripheral blood was obtained from adult healthy donors and anticoagulated with heparin. Buffy coats, PMN, peripheral blood mononuclear cells (PBMC), lymphocytes (PBL) and the NK cell subset were obtained as previously described in detail (10, 15). Monocytes were prepared from PBMC by adherence to plastic (45 min, 37° C.) and depleted of contaminating lymphocytes by complement (C)-dependent lysis (45 min, 37° C.) after treatment with a mixture of C-fixing antibodies anti-CD21, anti-CD16 and anti-CD3. Macrophages were collected after culturing this population for 10–12 days in RPMI-1640 supplemented with 10% human serum. Both NA-1 and NA-2 homozygous donors were used. To obtain large numbers of homogeneous CD3(−)/CD16(+) NK cells, PBMC were cocultured with 50 Gy-irradiated RPMI-8866 cells, as described (20). These 10-d cultures contain, on average, 80% CD3(−)/CD16(+)/NKH-1(+) NK cells and 20% CD3(+)/CD16(−)/NKH-1(−) T lymphocytes. The NK cells were purified by negative selection using anti-globulin rosetting and density gradient centrifugation after sensitization of the lymphocytes with a mixture of anti-CD3, anti-CD5 and anti-CD14 monoclonal antibodies. These NK cell populations have morphologic phenotypic and functional properties identical to those of NK cells freshly purified from blood (20,23). Like these cells, in vitro propagated NK cells express functional FcγRIII(CD16), but neither FcγRII (CD32) nor the high affinity receptor for the Fc fragment of monomeric IgG, FcγRI. The purity of each leukocyte preparation was tested by indirect immunofluorescence (flow cytometry) using anti-NK (anti-CD16 and anti-NKH-1), anti-T (anti-CD 3 and anti-CD5), anti-monocyte (anti-CD14) and anti-PMN (anti-CDw17) reagents. Purity always exceeded 95%.

Glycosyl-phosphatidyl inositol-specific phospholipase C (PI-PLC) treatment. PI-PLC purified from *Bacillus thuringiensis* was a kind gift of Dr. M. Low (Columbia University, New York, N.Y.). In a typical preparation, the enzyme had a specific activity of approximately 1700 u/ml. Cells ($5 \times 10^6$/ml RPMI-0.25% BSA) were treated with a 1:200 dilution of PI-PLC (45 min, 37° C.) and washed twice before testing. Cell viability after treatment was greater than 95% as judged by vital dye exclusion; no loss of specific cell subsets was ever detected as judged by surface marker analysis in indirect immunofluorescence.

Indirect immunofluorescence. This was performed as previously described in detail (10) using an FITC-goat F(ab')$_2$ anti-mouse Ig (Cooper) preabsorbed on human IgG. Irrelevant antibodies of matched isotypes were used as negative controls. The samples were analyzed on an Ortho Cytofluorograf 50H connected to a 2150 Data Handling System (Ortho Diagnostic Systems, Inc., Westwood, Mass.). Intensity of fluorescence was measured on a logarithmic scale.

Immunoprecipitation of FcγRIII(CD16) and N-glycanase treatment. Intact NK cells, purified by negative selection from either PBL or 10-d cocultures of PBMC with B lymphoblastoid cell lines and PMN from the same donors were labelled with $^{125}$I (Amersham International, Arlington Heights, Ill., 1mCi/10$^7$ cells using 1,3,4,6-tetrachloro-3α, 6α-diphenyglycuroil (100 μg/tube; Iodogen, Pierce Chemical Co., Rockford, Ill.). When indicated, $^{125}$I-labelled PMN and NK cells were incubated with PI-PLC as described above and both cell-free supernatants and cell pellets were used for immunoprecipitation. After washing, cells were lysed (20 min, 4° C.) with 1% Nonidet P-40, (NP-40, Calbiochem Behring Corp, LaJolla, Calif.) in 0.1M Tris pH6.8 containing 2 mM EDTA, 2 mM PMSF, 0.33 U/ml aprotinin, 15% glycerol; the cell lysate was centrifuged (13,000 rpm, 30 min) and the postnuclear supernatant was collected. All samples were preabsorbed (12h, 4° C.) with Streptavidin-agarose beads (Bethesda Research Laboratories, Gaithersburg, Md.) (25 μl beads/$5 \times 10^7$ cells) and mouse monoclonal IgG2a of no known antigen specificity (10 μg/$5 \times 10^7$ cells). Aliquots from the samples were sequentially incubated (3 h, 4° C. each incubation) with biotin-labeled anti-CD16 or irrelevant antibodies as control (5 μg/10$^7$ cells) and with Streptavidin-agarose (BRL) (10 μl beads/10$^7$ cells). The streptavidin-agarose beads were washed 5 times with 0.15 M NaCl containing 4 mM EDTA, 1 mM PMSF, 0.02% NaN$_3$, 10 mM Hepes, 0.1% Tween-20, pH 7.2. After boiling (5 min, 100° C.) in the presence of 0.5% SDS, 0.1 M 2-mercaptoethanol (2ME), each sample was treated with N-glycanase according to the manufacturer. Briefly, Na-phosphate buffer (0.17 M, pH 8.6), 10 mM 1,10 phenantroline (Sigma Chemical Co., St. Louis, Mo.) and 1% NP-40 were added to each sample before addition of N-glycanase (Genzyme, Boston, Mass.) (20 u/ml) to one of two identical aliquots. After 18-h incubation at 37° C., sample buffer (62.5 mM Tris pH 6.5 containing 12.5% glycerol, 1% 2-ME, 2.5% SDS, 0.005% bromophenol blue) was added and the samples were analyzed in SDS-10% polyacrylamide slab gel electrophoresis (PAGE) (24). Molecular weight markers (Pharmacia Fine Chemicals) were: α-lactalbumin, soybean trypsin inhibitor, carbonic anhydrase, ovalbumin, bovine serum albumin, and phosphorylase b for 14.4, 20.1, 30, 43, 67 and 94 kD, respectively. The gels were dried and exposed to Kodak Xomat X-ray films at −70° C. with Lightning Plus intensifying screens (DuPont Co., Wilmington, Del.).

RNA and DNA preparations. NK cells, PMN and macrophages were washed twice with cold phosphate buffered saline (PBS) and lysed with 4 M guanidine isothiocyanate for extraction of total cellular RNA after the centrifugation through CsCl$_2$ (25). Genomic DNA was prepared from spleen and placenta as previously described (26).

Oligonucleotides. All oligonucleotides were synthesized on an Applied Biosystems Model 381A. HPLC purification was performed according to ABI specifications or oligonucleotides were used without further purification; no differences were observed. The oligonucleotide primers and probes used were derived from the published cDNA sequence for FcγRIII(CD16) (7) and the numbering corresponds to that report.

```
Oligo 485: GAGAGGCCTGAGGATGAT (870-888);
complement

Oligo 491: GGTTGCAAATCCAGAGAA (850-868);
complement

Oligo 465: TCATTTGTCTTGAGGGTC (781-799);
complement

Oligo 474: TTTCTCCATTTAAGTTTA (761-779);
complement

Oligo 488: TTTCTCCATTTAAATTTA (761-779);
pos. 766
``` from NK

```
Oligo 489: ACAAACATTCGAAGCTCA (724-742); pos. 733
``` from NK

```
Oligo 490: ACAAACATTTGAAGCTCA (724-742)

Oligo 473: TGGTACTCCTTTTTGCAG (677-695)

Oligo 466: GTCTCTTTCTGCTTGGTG (658-676)

Oligo 501: AAGAACACTGCTCTGCAT (427-445)

Oligo 494: CACCTGAGGTGTCACAGC (406-424)

Oligo 492: TCTTTGGTGACTTGTCCA (1-18)
``` cDNA synthesis and PCR amplification. 10 ug of total RNA extracted from either PMN or NK cells were incubated in a reaction which contained either 0.5 or 50 pMoles of a 3' oligonucleotide primer (485 or 465), 20 units of MuMLV reverse transcriptase (Life Sciences), 200 uM of each dNTP, 50 mM KCl, 10 mM Tris-Cl, pH 8.3, 1.5 mM MgCl$_2$ and 0.01% gelatin. The reaction was allowed to proceed at 42° C. for 60 minutes after which time 0.5 or 50 pM of a 5' oligonucleotide primer (492, 494 or 466) was added along with 2.5 units of Taq polymerase (Cetus). 35 cycles of denaturation, annealing and extension were performed as described (27) in a Perkin Elmer Cetus DNA thermal cycler. Denaturation was at 94° C. for 1 minute, annealing was at 44° C. for 2 minutes and extension was at 72° C. for 3 minutes. A final cycle with a 7 minute extension was performed.

Preparation of $^{32}$P-labelled fragments and sequence analysis. Typically, 20% of a reaction described above was incubated with 5' end-labelled $^{32}$P oligonucleotide internal to the amplified segment of the cDNA, using 50 pM of labelled oligonucleotide. Extension was performed with Taq polymerase (Cetus) and one cycle of denaturation, annealing and extension. Denaturation was at 92° C. for 1 min, annealing was at 37° C. for 2 min and extension was at 72° C. for 10 min. The labelled product was purified on a 5% acrylamide/TBE gel, electroeluted and subjected to DNA sequencing using the chemical degradation method (28). Alternatively, the PCR products were cloned into pUC-18 and sequenced by dideoxy chain-termination (29).

Oligonucleotide hybridization of PCR amplified cDNAs.

cDNA from NK cells and PMN obtained from the same donor were synthesized and amplified using oligonucleotides 465/466, spotted on nitrocellulose membranes, denatured and baked as described (30). 5' end labelled oligonucleotides specific for NK cells (488, 489) or PMN (474, 490) sequences were hybridized and washed as described (31) at 5° C. below the calculated $T_m$.

Isolation of genomic clones for FcγRIII(CD16). EcoR1 digested placental DNA was size fractionated on a preparative agarose electrophoresis apparatus (Hoefer). The 9.0 kb fraction which hybridized with an FcγRIII(CD16) probe was cloned into the phage vector lambda CH28, packaged in vitro and plated on *E. coli* strain C600. Nine positive clones were obtained from 150,000 phage which were plaque purified and analyzed by restriction digestion, oligonucleotide hybridization and DNA sequence analysis. Similarly, an 18 kb BamH1 fraction, determined to hybridize with the FcγRIII(CD16) probe, was cloned with L47.1. Four positive phage were obtained from 250,000 plaques. Cosmid clones encoding these two genes were isolated from a human placenta cosmid library constructed in the vector pWE15 and generously provided by Dr. Glenn Evans (Salk Institute).

Results

Characterization of FcγRIII(CD16) on NK cells

Figure 1:
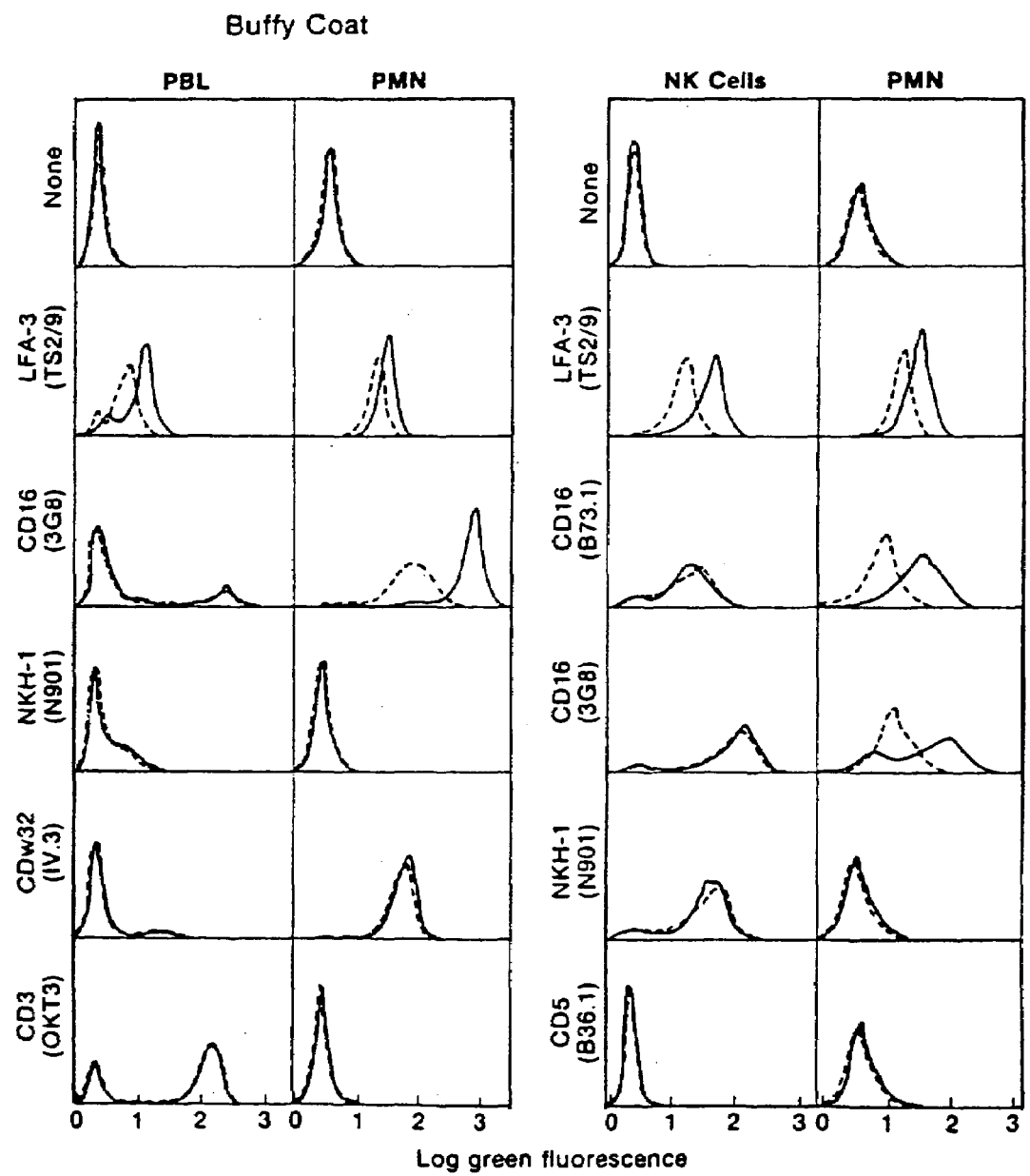
FIG. 1. FcγRIII(CD16) expression on NK cells and PMN.

To define the nature of the FcγRIII(CD16) anchor on NK cells, its presence on buffy coat cells was tested by indirect immunoflourescence after PI-PLC-treatment. Flourescence profiles obtained on the lymphocyte (PBL), in which only NK cells bear FcγRIII(CD16), and PMN populations in the same sample and gated on the basis of their light scatter characteristics are shown in FIG. 1. FcγRIII(CD16) fluorescence, as detected by mAb 3G8, was reduced on both buffy coat and purified PMN by approximately 85%, yet little or no decrease for this molecule was observed on PBL. As with fresh lymphocytes (left panel), little or no decrease of fluorescence for FcγRIII(CD16) was observed on PI-PLC treated NK cells purified by negative selection from 10-day co-cultures of peripheral blood mononuclear cells (PBMC) with irradiated B lymphoblastoid cell lines (FIG. 1, right panels). In contrast, PI-PLC reduced the fluorescence due to LFA-3 in both PMN and NK cell populations by approximately 53%. The insensitivity of FcγRIII(CD16) on NK cells, then, is not the result of an inability of these cells to express PI-linked molecules or their insensitivity to PI-PLC because of unique membrane properties of NK cells. These PI-PLC treated NK cells maintained their characteristic phenotype [NKH-1(+)/CD5(−)] and were still able to bind particulate immune complexes, (data not shown). These data indicate that FcγRIII(CD16) is resistant to PI-PLC when expressed on NK cells, yet is sensitive to this enzyme when expressed on PMN.

Biochemical characteristics of FcγRIII (CD16) precipitated from NK cells and PMN The biochemical basis for the altered PI-PLC sensitivity of FcγRIII(CD16) on NK cells was investigated by comparing the protein backbone of the molecule on NK cells and PMN. FcγRIII(CD16) was immunoprecipitated from PI-PLC treated Nk cells and PMN and from the medium in which they were maintained. The products were analyzed on SDS-PAGE after treatment with N-glycanase (FIG. 2). FcγRIII(CD16), which migrates as a broad band of apparent mass 50–70 kDa, was immunoprecipitated from control NK cells and PMN (FIG. 2, panel A). N-glycanase treatment of the immunoprecipitate from NK cells resulted in the appearance of two bands of 32 and 36 kDa apparent mass, with occasionally a less intense band at 38–40 kDa. In contrast, two bands of smaller mass, migrating between 23 and 28 kDa, were detected after N-glycanase treatment of the immunoprecipitate from PMN. PI-PLC treatment of NK cells resulted in equivalent amounts of immunoprecipitable FcγRIII(CD16) to those precipitated from untreated control NK cells, while no significant amount of immunoprecipitable protein remained on the PI-PLC-treated PMN (FIG. 2, panel B, cell pellets). In addition to the products described above, N-glycanase treatment generated bands of higher molecular mass which were observed whether N-glycanase digestion was prolonged up to 30 h and using concentrations of the enzyme as high as 40 U/ml (data not shown), as reported previously (11, 14). Although it is possible that the larger band within the precipitate from each cell type represents an incompletely deglycosylated peptide, in no instance were bands of molecular mass lower than 32 kDa or higher than 28 kDa precipitated from NK cells or PMN, respectively, in experiments performed with 8 different donors. A minimum difference of 4 kDa thus exists between the NK cell and PMN FcγRIII(CD16) proteins. Variable but significant amounts of FcγRIII(CD16) were reproducibly immunoprecipitated from the NK cell supernatant fraction (FIG. 2, panel B, supernatants) irrespective of PI-PLC treatment. This result was reproducibly obtained using freshly isolated NK cells or B73.1 antibody for FcγRIII (CD16) precipitation (data not shown). In agreement with a previous report (16) significant amounts of protein were also detected in the supernatant fraction from untreated PMN, which was more abundant in the supernatants from PI-PLC-treated PMN. N-glycanase treatment of the immunoprecipitates from supernatants of both NK cells and PMN resulted in two bands of 23 and 28 kDa apparent molecular mass irrespective of PI-PLC treatment. These results are in agreement with a previous study (7) showing that the FcγRIII (CD16) polypeptides precipitated from PI-PLC-treated NK cell supernatants, representing about 50% of those present on control cells, had apparent molecular mass of 28 kDa after N-glycanase treatment. Precipitation from NK cell pellets or control supernatants was not reported in that study. It is most likely that the soluble form of FcγRIII(CD16)

precipitated from the NK cell supernatants is not the result of PI-hydrolysis and, instead, derives from proteolytic cleavage of the molecule at a position, near the transmembrane domain, at which the molecule is processed in PMN during formation of the PI-anchor. A similar finding has been reported for the low affinity FcγRII. An IgE binding, 37 kDa molecule, detected in the supernatant of FcεRII expressing human B cells lines (32) arises by proteolytic degradation of a 45 kDa transmembrane form of FcεRII. These observations on the differences in the PI-PLC sensitivity and molecular weight after deglycosylation of FcγRIII(CD16) on NK cells and PMN promoted the inventors to characterize the FcγRIII(CD16) gene and its transcript in NK cells and PMN.

Analysis of FcγRIII(CD16) RNA in NK cells and PMN

Figure 3A:
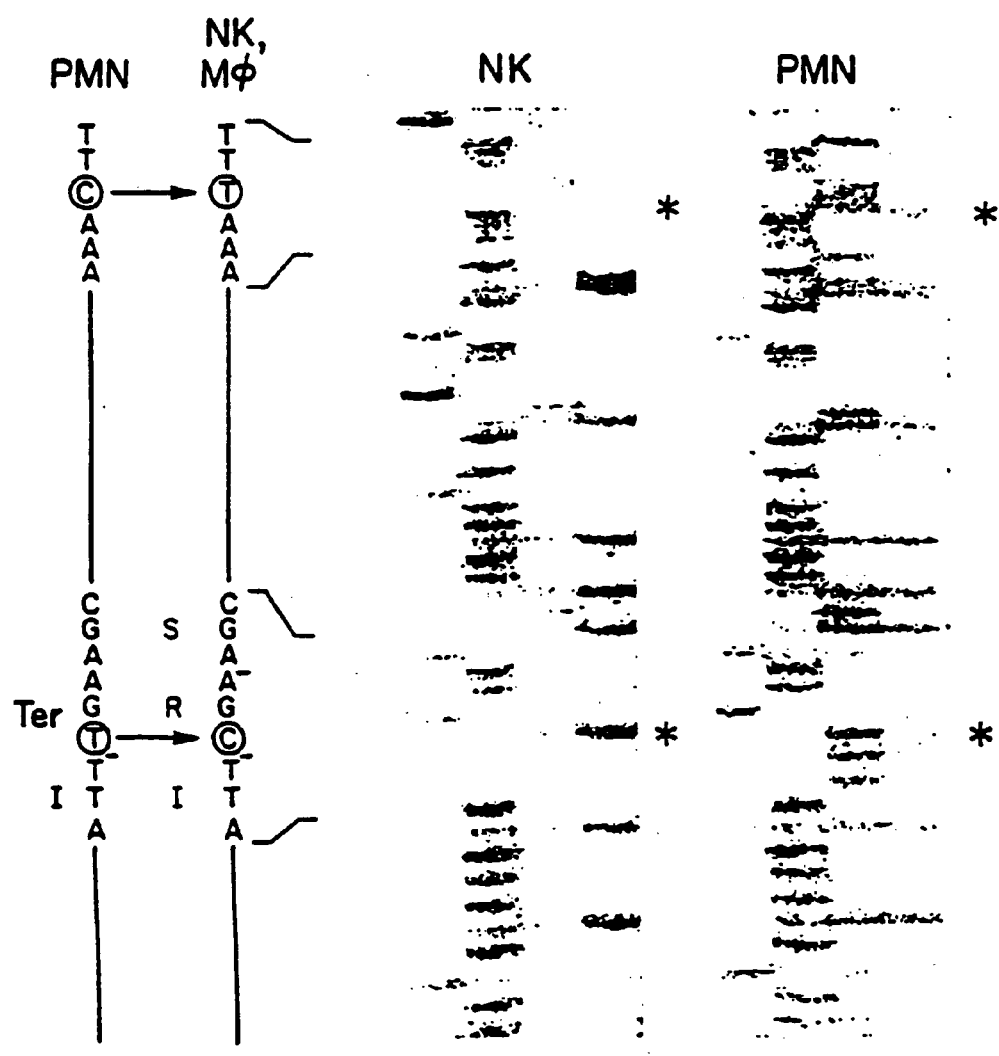

The molecular basis for the structural differences observed for FcγRIII(CD16) on PMN and NK cells was approached through the analysis of the RNA encoding these molecules. Northern blot analysis using FcγRIII(CD16) specific probes revealed a single species of identical size in PMN and NK cells (not shown). In a previous study (7), $S_1$ analysis demonstrated no detectable differences in the FcγRIII(CD16) encoding RNA obtained from NK cells as compared to a cDNA sequence encoding the PI-linked molecule. To determine the structural basis for the size difference of the deglycosylated proteins observed on PMN and NK cells, sequence analysis of cDNAs corresponding to these RNA was performed. Total RNA was extracted from both cell types obtained from an NA-2/NA-2 donor, converted to cDNA using FcγRIII(CD16) specific primers and reverse transcriptase and amplified by the polymerase chain reaction. Sequence analysis of those cDNA revealed single nucleotide substitutions in the NK cell transcript (corresponding to nucleotides 1–887). For example, as shown in FIG. 3A, a T at position 733 in the sequence derived from PMN RNA is seen to be a C in the sequence obtained from NK cell RNA, resulting in an extending open reading frame for the NK cell transcript. Similarly, a C at position 766 in PMN is found to be a T in NK cells. Sequence analysis of this region of the FcγRIII(CD16) RNA obtained from the cDNA amplified from these cell types of this donor revealed the following cell-type specific single nucleotide substitutions: position 141 (C to G), 147 (T to C), 277 (A to G), 473 (A to G), 505 (C to T), 531 (T to C), 559 (G to T), 641 (C to T), 733 (T to C), 766 (C to T), 814 (A to G) and 829 (G to A) (FIG. 3B). These 12 nucleotide changes result in 6 amino acid changes (FIG. 3B). Similar sequence analysis of transcripts derived from PMN and NK cells of a second donor (NA-1/NA-1) revealed the same nucleotide substitutions between NK cells and PMN at positions 473, 505, 531, 559, 641, 733, 766, 814 and 829 as were seen for the NA-2/NA-2 donor, revealing that these differences between NK cells and PMN were not the result of allelic variation. In contrast, 5 nucleotides were found to differ between PMN transcripts of NA-2 and NA-1 donors: positions 141 (C to G), 147 (T to G), 277 (A to G), 227 (G to A) and 349 (A to G) (bold-face nucleotides in III-1, FIG. 3B). No differences were detected in NK transcripts between NA-2 and NA-1, indicating that NA-1 and NA-2 alleles are restricted to III-1. The three nucleotide differences at positions N1, 147 and 277 coincide with the cell-type specific differences between III-1 and III-2 in the NA-2 homozygous donor, resulting in a III-1, NA-1 sequence identical to III-2 at those positions. This pattern of nucleotide substitution in III-1 for NA-1 and NA-2 allows for the mapping of these epitopes. Since NK cells are always NA-2 positive and do not express the NA-1 epitope we can conclude that the nucleotide differences at positions 227 and 349 must determine the NA-1 and NA-2 epitopes. The G to A transition in III-1, NA-1 at position 227 results in the loss of the glycosylation sequence Asn-Glu-Ser$^{65}$ in III-1, NA-2, converting it to Asn-Glu-Asn$^{65}$. Similarly, the A to G transition at position 349 in III-1, NA-1 results in an Ile$^{106}$ to Val$^{106}$ change.

The specificity of expression of the III-1 and III-2 transcripts was demonstrated by oligonucleotide hybridization oligonucleotide probes which differed only at a single nucleotide, indicated in FIG. 4, were hybridized to PCR amplified cDNA obtained from four sets of donor-matched aPMN and NK cells. In all cases, the NK cell derived RNA contain a C at position 733 and a T at position 766, while PMN have a T and C at these positions, respectively. An oligonucleotide probe common to both cell type transcripts hybridized to all samples. Hybridization and sequencing studies revealed no evidence for molecular heterogeneity within a single cell type.

Structural analysis of two FcγRIII(CD16) genes

The basis for these single nucleotide differences in FcγRIII(CD16) transcripts of NK cells and PMN was investigated by determining the gene structure for this receptor. Southern blot analysis of placenta or spleen DNA restricted with EcoR1, HindIII, NcoI, KpnI, BglIII, and PstI and probed with exon-specific probes for the signal sequence, the extracellular domains (encoded on two exons) or the transmembrane-cytoplasmic-3'UT exon all demonstrated single restriction fragments (not shown), suggestive of a single gene or two highly conserved genes. However, BamH1 revealed two restriction fragments of 4.8 kb and 18 kb when probed with either an EC-2 probe or TM-CYT-3'UT probe (FIG. 5). Similarly, HincII revealed two fragments of 5.0 and 3.0 kb when probed with this probe (not shown). To rule out polymorphism as the basis for these additional fragments, DNA from 23 individuals of different racial origins were restricted with HincII and probed with the FcγRIII(CD16) TM-CYT-3'UT probe. All DNAs revealed two distinct HincII fragments (not shown). These two distinct but highly homologous genes for FcγRIII (CD16) were cloned by size-fractionation of EcoR1 restricted placental DNA and cloning of the 9.0 kb fragment which encodes each FcγRIII(CD16) gene. Nine independent FcγRIII(CD16) clones were obtained which were screened with oligonucleotide probes described in FIG. 4 specific for each transcript. Five clones hybridized only with the NK-specific oligonucleotides while 4 clones hybridized exclusively with the PMN-specific oligonucleotides. In addition to these clones, the 18 kb BamH1 fragment shown in FIG. 5 was cloned and, as expected, hybridized only with the NK-specific oligonucleotide probes. Cosmid clones for each of these genes were also obtained. DNA sequence analysis of these two classes of clones confirmed the hybridization results. Gene III-1 encodes the PMN transcript sequence, while gene III-2 encodes the NK cell transcript sequence. The III-1 sequence determined demonstrates the 5 nucleotide substitutions in EC-1 characteristic of the NA-1 allele. Further evidence for a gene duplication for FcγRIII(CD16) was obtained by utilizing the observation that the nucleotide changes at position 733 and 766 each generate a novel restriction enzyme recognition site. The T to C change at 733 creates a Taq I site, while the C to T change at 766 creates Dra I site. As seen in FIG. 5, Taq I or Dra I digestion of spleen DNA hybridized with TM- or 3'UT probes reveals the existence of both sequences in the genome. When probed with the TM probe, Taq I reveals fragments of 6.5, 3.8, 3.5, kb (3.8 and 3.5 kb bands migrate as a doublet in this experiment) and 280 bp (seen optimally with the 3'UT probe), while Dra I generates fragments at 900, 550 and 350 bp. The 6.5 kb Taq I fragment seen in this experiment represents a polymorphism as determined by screening DNA obtained from individuals of different racial origins with Taq I. The 550 bp Dra I fragment is not detected when the 3'UT probe is used, since the probe is 3' of the expected fragment. The additional Taq and Dra fragments of 3.0 and 3.2 kb, respectively, detected with the 3'UT probe result from corresponding 3' fragments. Cloned genes specific for each transcript, when probed with the TM sequence, produce either a 3.8 kb Taq fragment (III-1) or a 3.5 kb and 0.28 kb fragment (III-2); Dra I reveals either a 900 bp fragment (III-1) or a 550 and 350 bp fragment (III-2). A map of these two genes, derived from hybridization and sequence analysis is presented in FIG. 5.

The nucleotide substitution at position 733 eliminates a translation termination sequence.

The nucleotide change at position 733 in gene III-2 occurs at a position in gene III-1 which specifies an in frame translation termination codon TGA (occuring after the codon for amino acid 238), encoding in its place a CGA codon that specifies the amino acid arginine. The resulting open reading frame for the transcript derived from III-2, shown in FIG. 6a, encodes an additional 21 amino acids, terminating at nucleotide 797. The predicted cytoplasmic domain for the FcγRIII(CD16) sequence transcribed from the III-2 gene in NK cells is 25 amino acids long. The 46 additional amino acids encoded by the transmembrane and cytoplasmic domains present in the III-2 transcript in NK cells could account for an additional 6,000 dalton of mass, as would be predicted for a transmembrane-anchored FcγRIII(CD16) protein of NK cells. This value is in agreement with the results presented in FIG. 2, indicating that FcγRIII(CD16) on NK cells is resistant to PI-PLC and migrates, when deglycosylated, as a protein of apparent mass 5–10,000 dalton larger than its PMN homologue. The homology between the FcγRIII(CD16) protein predicted for human NK cells and the murine FcγRII α molecule is increased by this extended open reading frame. The FcγRIII(CD16) sequence for the NK cell molecule now demonstrates homology to the mouse FcγRIIα moleule not only in its transmembrane domain, as has been observed (7), but in its cytoplasmic domain as well (FIG. 6b).

The Mechanism of Anchoring of FcγRIII(CD16) depends on a single amino acid.

The form of membrane-anchorage of FcγRIII(CD16) depends on the amino acid present at position 203 as shown in FIG. 3B. The PI-anchored III-1 protein contains serine at position 203, whereas the transmembrane-anchored III-2 protein contains phenylalanine at position 203. When the transcript encoding III-1 was altered to code for phenylalanine at 203, the protein exhibited transmembrane linkage. Conversely, when the III-2 transcript was altered to code for serine at position 203, the protein showed PI-linkage. Thus, serine at position 203 determines PI anchorage and phenylalanine at position 203 determines transmembrane anchorage.

Cell lines stably expressing the FcγRIII(CD16) protein from PMN and NK cells.

Cell lines have been established which stably express the FcγRIII(CD16) protein from PMN and NK cells. The coding sequences for the III-1 and III-2 genes, respectively were cloned into the expression vector pc EXV-3 (39) in which the SV40 early promoter is used to achieve transcription of the cloned sequences. Mouse L-cells and monkey COS cells were transfected with the plasmid constructs. Cells were cotransfected with pcEXV-3 containing the coding sequence for FcεRIγ. All of the cell lines were cotransfected with pGCcos3neo, which confers resistance to the drug G418 (41). After 10 days in G418-containing medium, colonies were screened by rosetting with human erythrocytes conjugated with the monoclonal antibody 3G8. Positive cells were cloned and tested for FcεRIII(CD16). Three mouse L-cell lines expressing, respectively, III-1, III-2 together with FcεR$_{17}$, and III-1 together with FcεRIγ, and three monkey COS cell lines expressing, respectively, III-1, III-2 together with FcεRIε, and III-1 together with FcεRγ. As shown in FIG. 7, III-2 is expressed only in the presence of the γ subunit of the FcεRI protein. A similar effect was observed for the expression of the murine FcγRIIα protein.

These cell lines may be used in a diagnostic assay for antibody-dependent enhancement (ADE) of HIV infectivity. A cell line expressing FcγRIII(CD16) may be contacted with serum from an individual suspected of containing antibodies which enhance HIV infection. Infection of the cell line with HIV indicates ADE infection by HIV.

Discussion

FcγRIII(CD16) of NK cells and PMN differ in their PI-PLC sensitivity and their apparent molecular weights after deglycosylation. Cell-type specific transcripts which differ by single nucleotide substitutions were found to encode these alternative forms of FcγRIII(CD16). Numerous examples of alternative splicing to generate alternatively anchored or secreted proteins have been described (N-CAM, DAF, AchE and LFA-3; reviewed in 17). The molecular basis for the structural differences between the FcγRIII (CD16) molecule on PMN and NK cells is the result of cell-type specific transcription of nearly identical but distinct genes which encode these single nucleotide differences.

cDNA for FcγRIII(CD16) expressed in NK cells and PMN were synthesized and then amplified by the polymerase chain reaction. These sequences were found to differ by multiple single nucleotide substitutions found in regions of the molecule corresponding to the extracellular domain and transmembrane-cytoplasmic-3'UT regions. That these differences were observed consistently in only one (NK) of the paired RNA (NK/PMN) samples processed simultaneously argue against reverse transcriptase or PCR amplification as the source of these differences. Polymorphism has been reported to be associated with FcγRIII(CD16) on PMN. Two allelic forms (NA-1 and NA-2) have been described which are distinguished by human alloantisera, by molecular mass in SDS-PAGE and by specific monoclonal antibodies (21). Five nucleotide changes in the EC-1 domain of the III-1 gene are associated with allelic forms of the molecule, two of which are specific for the NA-1 or NA-2 alleles (227 and 349). The FcγRIII(CD16) protein immunoprecipitated from NA-2 homozygous donors migrates more slowly on SDS-PAGE as compared to NA-1 allele. The Ser$^{65}$ to Asn$^{65}$ change which results in the loss of a glycosylation site in NA-1 is therefore consistent with Ser$^{65}$ determining the NA-2 allele. The Val$^{106}$, then, is a likely candidate for the NA-1 determinant. The remainder of the changes were observed in different cell types of the same individual and were consistently observed in all NK cell samples, regardless of donor allele. Two genes encoding FcγRIII(CD16) were cloned and characterized. Both genes are encoded on human chromosome 1, tightly linked to FcγRII (CD32) genes and each other (Qiu and Ravetch, unpublished observations). These genes have nearly identical restriction maps and encode all the sequence differences observed between the NK cell and PMN transcripts for the appropriate allele. The 6.5 kb Taq polymorphism was not detected for a cosmid clone encoding the III-1 gene of the NA-1 allele (FIG. 5), raising the possibility that this polymorphism is associated with the III-1, NA-2 allele. The non-allelic nucleotide differences between III-1 and III-2 occur in all exons encoding the receptor, ruling out alternative splicing as the mechanism generating the alternative anchored forms of this receptor. However, the degree of identity between these genes is remarkable. This high degree of identity sugggests either a recent evolutionary history or a mechanism like gene conversion which maintains sequence fidelity.

Cell-type specific transcription of these two genes —III-1 in PMN and III-2 in NK cells appears to be exclusive (FIG. 4) and results in the appearance of alternatively anchored forms of FcγRIII(CD16) protein. The basis for this alternative anchoring results from the differences between these two genes and their respective transcripts. The III-1 gene encodes a transcript with a short (4 amino acid) cytoplasmic domain, which is expressed as a PI-anchored protein both in PMN and transfected COS cells. III-2 gene encodes a transcript with a cytoplasmic domain of 25 amino acids as a result of a T to C substitution in the termination codon TGA of the III-1 gene. The effect of this longer cytoplasmic domain is likely to contribute to the processing of this protein from a PI-linked molecule to a transmembrane protein. This hypothesis is supported by our studies on murine FcγRIIα, which is homologous to the FcγRIII (CD16) predicted for NK cells in its transmembrane and cytoplasmic domains. Murine FcγRIIα can be transfected and expresxsed in murine L cells (33), which do not express PI-linked molecules (34). In addition, we have observed that FcγRIIα is expressed as a PI-PLC resistant molecule on mouse macrophage cell lines (Zalman and Ravetch, unpublished) and NK cells (35).

Possible functions for the alternatively anchored forms of FcγRIII(CD16).

FcγRIII(CD16) has been postulated to mediate different functions on NK cells and PMN. This FcγR on NK cells mediates ADCC; the interaction of FcγRIII(CD16) with ligand on NK cells results in transduction of intracellular signals, presumably through its intracytoplasmic domain, that induce activation of genes for lymphokines and receptors involved in NK cell functions and biology (23, 36). This activation is mediated, at least partly, through increased $[Ca^{2+}]$ i and receptor-induced phosphatidylinositol hydrolysis. The role of FcγRIII(CD16) on PMN is less certain. Those cells express two distinct classes of receptors for immune complexes, FcγRII (CD32) and FcγRIII(CD16). Antibodies to either FcγR class inhibit PMN functions, suggesting that both receptors may be needed to trigger a functional response and may act synergistically when presented with multivalent immune complexes. Since PMN anchor FcγRIII(CD16) with a PI tail attachment, it has been proposed that the role of this form of the molecule is to capture immune complexes without triggering neutrophil activation (13). The cell-type specific expression of the two genes encoding FcγRIII(CD16) described here which generates these alternative protein forms thus has a significant effect on the biological function of these molecules.

REFERENCES

1. Unkeless, J. C., Scigliano, E., and Freedman, V. H. (1988) Structure and function of human and murine receptors for IgG. Ann. Rev. Immunol. 6, 251–281.
2. Ravetch, J. V., Luster, A. D., Weinshank, R., Kochan, J., Pavlovec, A., Portnoy, D. A., Hulmes, J., Pan, Y-C., and Unkeless, J. C. (1986) Structural heterogeniety and functional domains of murine immunoglobulin G Fc receptors. Science 234, 718–725.
3. Lewis, V. A., Koch, T., Plutner, H., and Mellman, I. (1986) A complementary cDNA clone for a macrophage-lymphocyte Fc receptor. Nature 324, 372–375.
4. Hogarth, P. M., Hibbs, M. L., Bonadonna, L., Scott, B. M., Witort, E., Pieterz, G. A., and McKenzie, I. (1987) The mouse Fc receptor for IgG (Ly-17): molecular cloning and specificity. Immunogenetics 26, 161–168.
5. Stuart, S. G., Trounstine, M. L., Vaux, D. J. T., Koch, T., Martens, C. L., Mellman, I., and Moore, K. W. (1987) Isolation and expression of cDNA clones encoding a human receptor for IgG (FcγRII). J. Exp. Med. 166, 1668–1684.
6. Stengelin, S., Stamenkovic, I., and Seed, B. (1988) Isolation of cDNAs for two distinct human Fc receptors by ligand affinity cloning. EMBO. J. 7, 1053–1059.
7. Simmons, D., and Seed, B. (1988) The Fc receptors of natural killer cells is a phospholipid-linked membrane protein. Nature 333, 568–570.
8. Peltz, G. A., Grundy, H. O., Lebo, R. V., Yssel, H., Barsh, G. S. and Moore, K. W. (1989) Human FcγRIII: cloning, expression and identification of the chromosomal locus of two Fc receptors for IgG. Proc. Natl. Acad. Sci. USA 86, 1013–1017.
9. Fleit, H. G., Wright, S. D., and Unkeles, J. C. (1982) Human neutrophil Fc receptor distribution and structure. Proc. Natl. Acad. Sci. USA 79, 3275–3279.
10. Perussia, B., Acuto, O., Terhorst, C., Faust, J., Lazarus, R., Fanning, V., and Trinchieri, G. (1983) Human natural killer cells analyzed by B73.1, a monoclonal antibody blocking FcR functions. II. Studies of B73.1 antibody-antigen interaction on the lymphocyte membrane. J. Immunol. 130, 2142–2148.
11. Clarkson, S. B., and Ory, P. A. (1988) CD16 Developmentally regulated IgG Fc receptors on cultured human monocytes. J. Exp. Med. 167, 408–417.
12. Titus, J. A., Perez, P., Kaubisch, A., Garrido, M. A., and Segal, D. M. (1987) Human K/natural killer cells targeted with hetero-cross-linked antibodies specifically lyse tumor cells in vitro and prevent tumor growth in vivo. J. Immunol 139, 3153–3158.
13. Selvaraj, P., Rosse, F., Silber, R., and Springer, T. A. (1988) The major Fc receptor in blood has a phosphatidylinositol anchor and is deficient in paroxysmal nocturnal haemoglobinuria. Nature 333, 565–567.
14. Lanier, L. L., Ruitenberg, J. J., and Phillips, J. H. (1988) Functional and biochemical analysis of CD16 antigen on natural killer cells and granulocytes. J. Immunol. 141, 3478–3485.
15. Perussia, B., Trinchieri, G., Jackson, A., Warner, N. L., Faust, J., Rumpold, H., Kraft, D., and Lanier, L. L. (1984) The Fc receptor for IgG on human natural killer cells: phenotypic, functional and comparative studies using monoclonal antibodies. J. Immunol. 133, 180–189.
16. Huizinga, T. W. J., Van Der Schoot, C. E., Jost, C., Klaassen, R., Kleijer, M., Von Dem Borne, A. E. G. K., Ross, D., and Tetteroo, P. A. T. (1988) The PI-linked receptor FcRIII is released on stimulation of neutrophils. Nature 333, 667–669.
17. Ferguson, M. A. J., and Williams, A. F. (1988) Cell-surface anchoring of proteins via glycosyl-phosphatidylinositol structures. Ann. Rev. Biochem. 57, 285–320.
18. Yoda, Y., and Abe, R. (1985) Deficient natural killer (NK) cells in paroxysmal nocturnal haemoglobinuria (PNH): studies of lymphoid cells fractionated by discontinuous density gradient centrifugation. Br. J. Haematol. 60, 669–675.
19. Low, M. G. (1987) Biochemistry of the glycosyl-phosphatidylinositol membrane protein anchors. Biochem. J. 244, 1–13.
20. Perussia, B., Ramoni, C., Anegon, I., Cuturi, M. C., Faust, J., and Trinchieri, G. (1987) Preferential proliferation of natural killer cells among peripheral blood mononuclear cells cocultured with B lymphoblastoid cell lines. Nat. Immun. Cell Growth Regul. 6, 171–188.
21. Tetteroo, P. A. T., Van Der Schoot, C. E., Visser, F. J., Bos, M. J. E., and Von Dem Borne, A. E. G. Kr. (1987) Three different types of Fc receptors on human leucocytes defined by workshop antibodies; $FcγR_{low}$ of neutrophils, $FcγR_{low}$ of KINK lymphocytes, and FcγRII. In: Leucocyte Typing III, McMichael, A. J., ed., Oxford University Press, Oxford, England. pp. 702–706.
22. Sanchez-Madrid, F., Krensky, A. M., Ware, C. F., Robbins, E., Strominger, J. J., Burakoff, S. J., and Springer, T. A. (1982) Three distinct antigens associated with human T lymphocyte-mediated cytolysis: LFA-1, LFA-2, and LFA-3. Proc. Natl. Acad. Sci. USA 79, 7489–7493.
23. Anegon, I., Cuturi, M. C., Trinchieri, G., and Perussia, B. (1988) Interaction of Fcγ receptor (CD16) with ligands induces transcription of IL-2 receptor (CD25) and lymphokine genes and expression of their products in human natural killer cells. J. Exp. Med. 167, 452–472.
24. Laemmli, U. K., 1970. Cleavage of structural proteins during the assembly of the head of bacteriophage T4. Nature 227, 680–685.
25. Chirgwin, J. J., Przbyla, A. E., MacDonald, R. J., and Rutter, W. J. (1979) Isolation of biologically active ribonucleic acid from sources enriched in ribonuclease. Biochemistry 18, 5294–5299.
26. Ausubel, F. M., Brent, R., Kingston, R. E., Moore, D. D., Seidman, J. C., Smith, J. A. Struhl, K. (1987) In: Current Protocols in Molecular Biology. (New York: Greene Publishing Associates and John Wiley and Sons).
27. Saiki, R. K., Gelfand, D. H., Stoffel, S., Scharf, S. J., Higuchi, R. Horn, G. T., Mullis, K. B., and Erlich, H. A. (1988) Primer-directed enzymatic amplification of DNA with a thermostable DNA polymerase. Science 239, 487–491.
28. Maxam, A. M., and Gilbert, W. (1980) Sequencing end-labelled DNA with base-specific chemical cleavages. Meth. Enzymol. 65, 499–560.
29. Sanger, F., Nicklen, S., and Coulson, A. R. (1977) DNA sequencing with chain terminating inhibitors. Proc. Natl. Acad. Sci. USA 74, 5463–5467.
30. Southern, E. M. (1975) Detection of specific sequences among DNA fragments separated by gel electrophoresis. J. Mol. Biol. 98, 503–517.
31. Zeff, R. A., Gopas, J., Steinhauer, E., Rajan, T. V., and Nathenson, S. G. (1986) Analysis of somatic H-2 variants to define the structural requirements for Class I antigen expression. J. Immunol. 137, 897–903.
32. Letellier, M., Nakajima, T., and Delespesse, G. (1988) IgE receptor on human lymphocytes. IV. Further analysis of its structure and of the role of N-linked carbohydrates. J. Immunol. 141, 2374–2381.
33. Weinshank, R. L., Luster, A. D., and Ravetch, J. V. (1988) Function and regulation of a murine macrophage-specific IgG Fc receptor, FcγR-α. J. Exp. Med. 167, 1909–1925.
34. Waneck, G. L. Stein, N. E., and Flavell, R. A. (1988) Conversion of a PI-anchored protein to an integral membrane protein by a single amino acid mutation. Science 241, 697–699.
35. Perussia, B., Tutt, N. M., Qiao, W. Q., Kuziel, W. A., Tucker, P. W., Trinchieri, G., Bennett, M., Ravetch, J. V., and Kumar, V. (1989) Murine natural killer cells express functional Fcγ receptor II encoded by the FcγRα gene. J. Exp. Med. 170, 73–86.
36. Cassatella, M. A., Anegon, I., Cuturi, M. C., Griskey, P., Trinchieri, G., and Persussia, B. (1989) FcγR(CD16) interaction with ligand induces $Ca^{2+}$ mobilization and phosphoinositide turnover in human natural killer cells. Differential role of $Ca^{2+}$ in FcγR(CD16) and IL-2-induced transcription and expression of lymphokine genes. J. Exp. Med., 169, 549–568.
37. Lipman, D. J., and Pearson, W. R. (1985) Rapid and sensitive protein similarity searches. Science 9227, 1435–1441.
38. Scallon, B. J., et al. (1989) A human immunoglobulin G receptor exists in both polypeptide-anchored and phosphatidylinositol-glycan-anchored forms. Proc. Natl. Acad. Sci. USA 86, 5079–5083.
39. J. Miller, et al., J. Immunol. 134, 4212 (1985).
40. Homsy, J., et al., The Fc and not CD4 Receptor Mediates Antibody Enhancement of HIV Infection in Human Cells (1989) Science 244, 1357–1360.
41. J. Southern et al., J. Mol. Appl. Genet. 1, 327 (1982).

The invention claimed is:

1. An isolated nucleic acid molecule, wherein the nucleic acid molecule encodes an Fc receptor protein III-2, the amino acid sequence of which is set forth in FIG. 3B.

2. An isolated nucleic acid molecule of claim 1 wherein the isolated nucleic acid molecule is a cDNA molecule.

3. An isolated nucleic acid molecule of claim 1, wherein the nucleic acid molecule is an RNA molecule.

4. A recombinant cloning vehicle comprising a cloning vector comprising DNA encoding an Fc receptor protein which is expressed on NK cells and macrophages wherein the DNA encoding an Fc receptor protein on NK cells has the nucleotide sequence set forth in FIG. 3B and which is designated III-2.

5. A recombinant cloning vehicle of claim 4 wherein the cloning vector is a plasmid.

6. A host cell comprising the recombinant cloning vehicle of claim 4.

7. An isolated nucleic acid molecule encoding a transmembrane form of FcγRIII, wherein said nucleic acid molecule comprises an alteration in the termination codon at nucleotides 733–735 of FIG. 3B designated III-1, to a coding codon, extending the reading frame to encode a larger cytoplasmic domain.

8. The isolated nucleic acid of claim 7, wherein the nucleic acid is a cDNA molecule and the alteration is a C to T transition mutation at nucleotide 733.

9. An isolated nucleic acid molecule of claim 7, wherein the nucleic acid molecule is an RNA molecule and the termination codon is altered from UGA to CGA.

10. The isolated nucleic acid of claim 7, wherein the cytoplasmic domain is extended by 21 amino acids.

11. The isolated nucleic acid molecule of claim 10, wherein the larger cytoplasmic domain has the following amino acid sequence:

K T N I R S S T R D W K D H K F K W R K D P Q D K.

12. A recombinant cloning vehicle comprising a cloning vector comprising DNA encoding an Fc receptor protein which is expressed on NK cells and macrophages wherein the DNA encoding the Fc receptor protein on NK cells has a nucleotide sequence which comprises a mutation resulting in alteration of a UGA termination codon to a CGA codon at nucleotides 733–735 of FIG. 3B designated III-1, extending the reading frame to encode a larger cytoplasmic domain.

13. A recombinant cloning vehicle of claim 12 wherein the cloning vector is a plasmid.

14. A host cell comprising the recombinant cloning vehicle of claim 13.

* * * * *